(12) United States Patent
Masubuchi et al.

(10) Patent No.: US 11,328,812 B2
(45) Date of Patent: May 10, 2022

(54) MEDICAL IMAGE PROCESSING APPARATUS, MEDICAL IMAGE PROCESSING METHOD, AND STORAGE MEDIUM

(71) Applicant: Canon Medical Systems Corporation, Otawara (JP)

(72) Inventors: Nozomi Masubuchi, Nasushiobara (JP); Ryo Shiraishi, Nasushiobara (JP); Takuya Sakaguchi, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 127 days.

(21) Appl. No.: 16/683,393

(22) Filed: Nov. 14, 2019

(65) Prior Publication Data

US 2020/0160981 A1 May 21, 2020

(30) Foreign Application Priority Data

Nov. 15, 2018 (JP) .............................. JP2018-214752

(51) Int. Cl.
| | | |
|---|---|---|
| *G16H 30/40* | (2018.01) | |
| *G16H 50/20* | (2018.01) | |
| *G06N 20/00* | (2019.01) | |
| *G06N 3/08* | (2006.01) | |
| *G06T 7/00* | (2017.01) | |

(52) U.S. Cl.
CPC .............. *G16H 30/40* (2018.01); *G06N 3/08* (2013.01); *G06N 20/00* (2019.01); *G06T 7/0012* (2013.01); *G16H 50/20* (2018.01); *G06T 2207/20081* (2013.01); *G06T 2207/30096* (2013.01)

(58) Field of Classification Search
CPC ........ G16H 30/40; G16H 50/20; G06N 20/00; G06N 3/08; G06T 7/0012; G06T 2207/20081; G06T 2207/30096
See application file for complete search history.

(56) References Cited

U.S. PATENT DOCUMENTS

| | | | |
|---|---|---|---|
| 2015/0254555 A1* | 9/2015 | Williams, Jr | G06N 3/0454 706/14 |
| 2018/0060512 A1* | 3/2018 | Sorenson | G06Q 10/06398 |
| 2018/0268737 A1* | 9/2018 | Garnavi | G06N 3/084 |
| 2018/0285773 A1* | 10/2018 | Hsiao | G06N 20/00 |
| 2019/0026608 A1* | 1/2019 | Hsieh | G06N 3/04 |
| 2019/0171914 A1* | 6/2019 | Zlotnick | G06F 3/0488 |

FOREIGN PATENT DOCUMENTS

| | | |
|---|---|---|
| JP | 2009-282686 A | 12/2009 |
| JP | 2013-25745 A | 2/2013 |
| JP | 2018-55376 A | 4/2018 |

* cited by examiner

*Primary Examiner* — Vu Le
*Assistant Examiner* — Julius Chai
(74) *Attorney, Agent, or Firm* — Oblon, McClelland, Maier & Neustadt, L.L.P.

(57) ABSTRACT

According to one embodiment, a medical image processing apparatus of an embodiment includes an acquirer, a reliability setter and a learner. The acquirer acquires training data created by a creator on the basis of a medical image. The reliability setter sets, to the training data acquired by the acquirer, reliability information based on a creation situation of the training data or information about the creator who created the training data. The learner generates a learned model using the training data according to weighting based on the reliability information set by the reliability setter.

16 Claims, 13 Drawing Sheets

154

| DOCTOR ID | NAME | AGE | NUMBER OF YEARS OF EXPERIENCE | TECHNICAL SCORE | QUALIFI-CATION | ATTENDANCE INFORMATION | ... |
|---|---|---|---|---|---|---|---|
| D001 | *** | *** | *** | *** | *** | *** | ... |
| D002 | *** | *** | *** | *** | *** | *** | ... |
| ... | ... | ... | ... | ... | ... | ... | ... |

| TRAINING DATA ID | MEDICAL IMAGE | LABEL INFOR- MATION | OPERATION SITUATION ||||| CREATOR INFORMATION ||||
|---|---|---|---|---|---|---|---|---|---|---|---|
| | | | TIME RE- QUIRED FOR CREATION | CONFIDENCE DEGREE | FRESHNESS DEGREE | QUALITY | NUMBER OF YEARS OF EXPERIENCE | TECHNICAL SCORE | QUALIFI- CATION | BUSYNESS DEGREE | |
| *** | **** | **** | **** | **** | **** | **** | **** | **** | **** | **** | ⋮ |
| ⋮ | ⋮ | ⋮ | ⋮ | ⋮ | ⋮ | ⋮ | ⋮ | ⋮ | ⋮ | ⋮ | ⋮ |

| TIME REQUIRED FOR CREATION | WEIGHT SCORE |
|---|---|
| INSUFFICIENT | 1 |
| SLIGHTLY INSUFFICIENT | 2 |
| SUFFICIENT | 3 |
| MORE THAN SUFFICIENT | 4 |
| ... | ... |

| TIME REQUIRED FOR CREATION | NUMBER OF YEARS OF EXPERIENCE | WEIGHT SCORE |
|---|---|---|
| SUFFICIENT | 0 TO 1 YEARS | 1 |
| | 1 TO 3 YEARS | 2 |
| | 3 TO 5 YEARS | 3 |
| | 5 YEARS OR LONGER | 4 |
| ... | ... | ... |

| TRAINING DATA ID | MEDICAL IMAGE | LABEL INFOR- MATION | OPERATION SITUATION SCORE ||||| CREATOR INFORMATION SCORE ||||
|---|---|---|---|---|---|---|---|---|---|---|---|
| | | | TIME RE- QUIRED FOR CREATION | CONFIDENCE DEGREE | FRESHNESS DEGREE | QUALITY | | NUMBER OF YEARS OF EXPERIENCE | TECHNICAL SCORE | QUALIFI- CATION | BUSYNESS DEGREE |
| *** | *** | *** | 3 | 2 | 2 | 5 | | 5 | 5 | 5 | 3 |
| ⋮ | ⋮ | ⋮ | ⋮ | ⋮ | ⋮ | ⋮ | | ⋮ | ⋮ | ⋮ | ⋮ |

158

| TRAINING DATA ID | MEDICAL IMAGE | LABEL INFORMATION | SUPPLEMENTARY INFORMATION | | | | ... |
| --- | --- | --- | --- | --- | --- | --- | --- |
| | | | TIME REQUIRED FOR CREATION | FRESHNESS DEGREE | QUALITY | DOCTOR INFORMATION | |
| \*\*\* | \*\*\* | \*\*\* | \*\*\* | \*\*\* | \*\*\* | \*\*\* | ... |
| ... | ... | ... | ... | ... | ... | ... | ... |

MEDICAL IMAGE PROCESSING APPARATUS, MEDICAL IMAGE PROCESSING METHOD, AND STORAGE MEDIUM

CROSS-REFERENCE TO RELATED APPLICATION

The present application claims priority based on Japanese Patent Application No. 2018-214752, filed on Nov. 15, 2018, the content of which is incorporated herein by reference.

FIELD

Embodiments described herein relate generally to a medical image processing apparatus, a medical image processing method, and a storage medium.

BACKGROUND

Conventionally, application of a machine learning technology in the medical field has been commercialized. Conventional learning in accordance with machine learning technology is based on the premise that a sufficient amount of training data (ground truth (GT) data) is collected in advance and training data with poor quality is not used. However, training data items in the medical field are important because they are few in number and are subject to many constraints such as a small number of patients and a necessity of training data to be created under the supervision of doctors. Further, such training data is created at a plurality of sites and by a plurality of doctors in many cases, and the quality of training data collected from a plurality of sources (medical institution terminals, and the like) may not be consistent.

BRIEF DESCRIPTION OF THE DRAWINGS

FIG. 5 is a diagram showing an example of details of training data with reliability of the first embodiment.

FIG. 6 is a diagram showing an example of details of a weighting table of the first embodiment.

FIG. 7 is a diagram showing an example of a weighting table for a plurality of items of the first embodiment.

FIG. 8 is a diagram showing an example of details of weighted training data of the first embodiment.

DETAILED DESCRIPTION

According to one embodiment, a medical image processing apparatus of an embodiment includes an acquirer, a reliability setter and a learner. The acquirer acquires training data created by a creator on the basis of a medical image. The reliability setter sets, to the training data acquired by the acquirer, reliability information based on a creation situation of the training data or information about the creator who created of the training data. The learner generates a learned model using the training data according to weighting based on the reliability information set by the reliability setter.

Hereinafter, a medical image processing apparatus, a medical image processing method, and a storage medium of embodiments will be described with reference to the drawings.

First Embodiment

Figure 1:
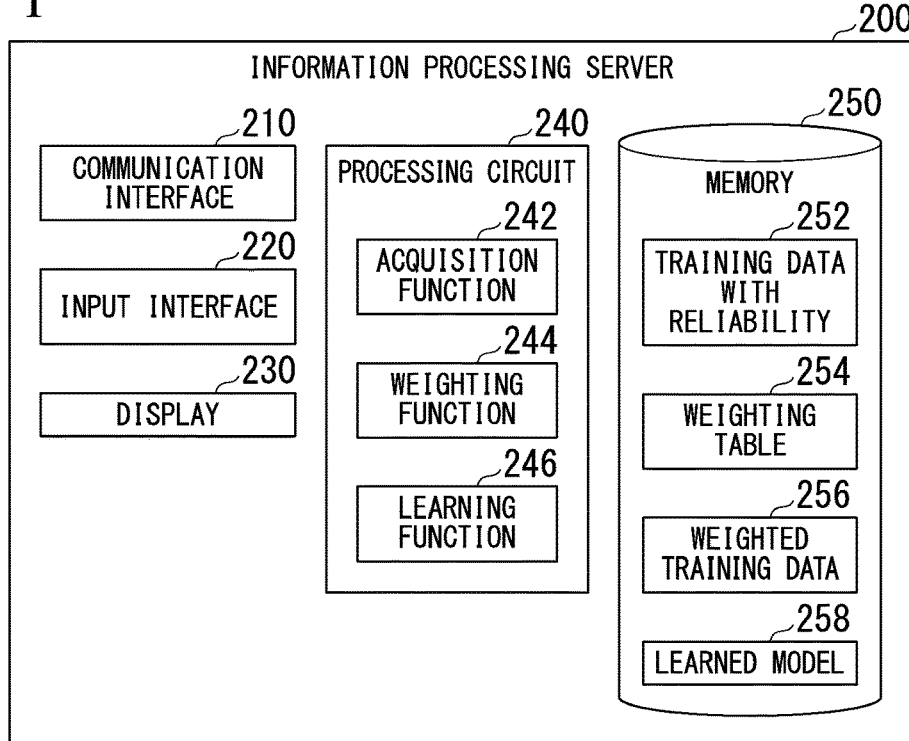
FIG. 1 is a diagram showing an example of a medical image processing system including a medical image processing apparatus of a first embodiment.
Figure 1:
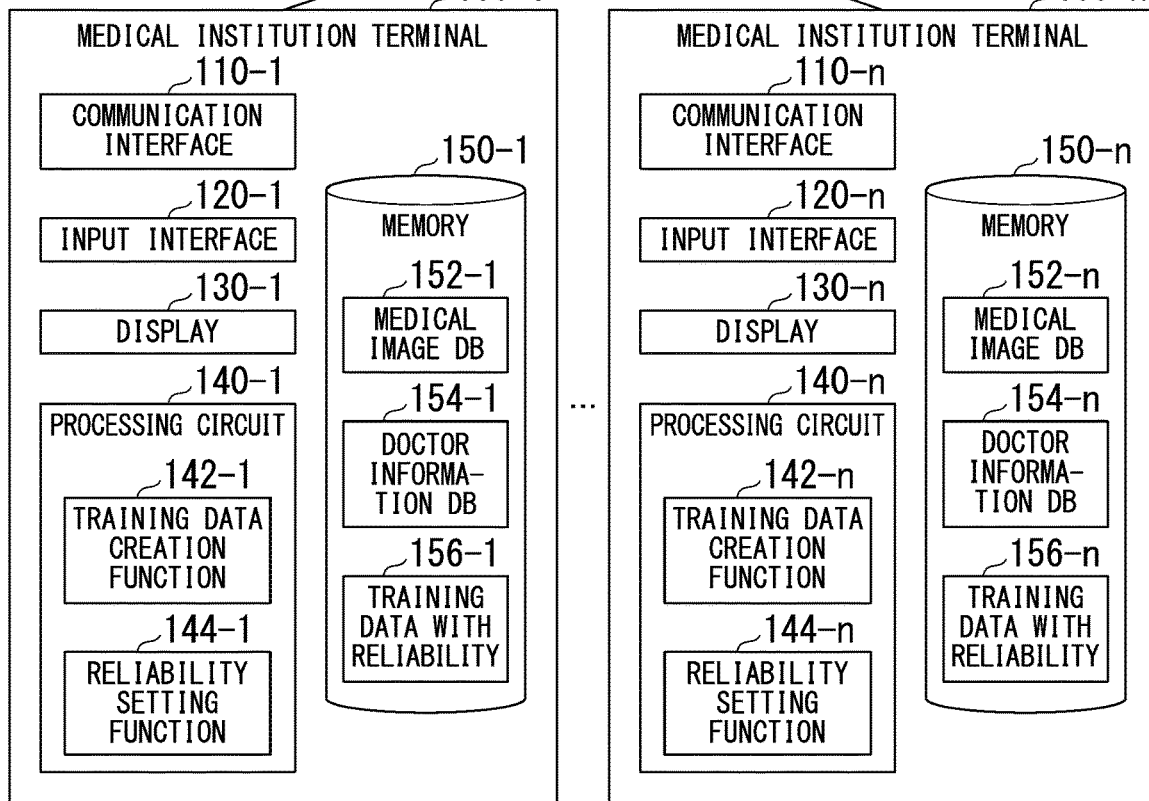

FIG. 1 is a diagram showing an example of a medical image processing system 1 including a medical image processing apparatus of a first embodiment. The medical image processing system 1 includes, for example, one or more medical institution terminals 100-1 to 100-n and an information processing server 200. The medical institution terminals 100-1 to 100-n and the information processing server 200 are connected, for example, through a network (NW) such as a wide area network (WAN), a local area network (LAN), the Internet, a dedicated line, a wireless base station, and a provider. In the following description, the medical institution terminals 100-1 to 100-n are collectively referred to as a "medical institution terminal 100" while omitting the symbols following the hyphens which identify the medical institution terminals when the medical institution terminals are not distinguished. In addition, the same applies to other components which are described using hyphens. In the first embodiment, the medical institution terminal 100 is an example of a "medical image processing apparatus."

The medical institution terminal 100 may be a computer included in a cloud computing system or a computer operating alone without depending on other apparatuses. The medical institution terminal 100 is, for example, a terminal provided in any of various medical facilities such as a diagnosis center, a hospital and a clinic, or a terminal owned by a doctor or the like belonging to any of various medical facilities. The medical institution terminal 100 receives an instruction such as a label with respect to a medical image and creates training data of the medical image using the received label. A medical image is obtained, for example, by imaging a result of photographing or measuring a portion of a human body for medical treatment or medicine. Medical images include computed tomography (CT) images, magnetic resonance (MR) images, mammography images, endoscopy images, X-ray images, etc. Further, medical images may be 2-dimensional images or 3-dimensional images. For example, medical images may be acquired from a medical image generation apparatus (not shown) installed in a medical facility in which the medical institution terminal 100 is provided or an external apparatus connected to the network NW.

Medical image generation apparatuses include, for example, a magnetic resonance imaging (MRI) apparatus, a CT apparatus, a mammography apparatus, an endoscopic image generation apparatus, an X-ray image generation apparatus, etc. An MRI apparatus generates an MR image, for example, by applying magnetic fields to a test object (e.g., a human body), receiving electromagnetic waves generated from hydrogen nuclei in the test object according to nuclear magnetic resonance using a coil and reconstructing a signal based on the received electromagnetic waves. A CT apparatus generates a CT image, for example, by radiating X rays to a test object from an X-ray tube rotating around the test object, detecting X rays that have passed through the test object and reconstructing a signal based on the detected X rays. A mammography apparatus generates a mammographic image, for example, by radiating X rays to the mamma of a test object and detecting X rays that have passed through the mamma. An endoscopic image photographing apparatus generates an endoscopic image of a predetermined portion in a body, for example, by inserting an endoscopy camera to a region near the predetermined portion and photographing the region near the portion.

An X-ray image generation apparatus generates an X-ray image, for example, by placing a test object between an X-ray radiation apparatus and a film and imaging the test object through printing.

In addition, the medical institution terminal 100 generates training data with reliability which is obtained by giving a reliability to training data and outputs the generated training data with reliability to the information processing server 200. Functions of the medical institution terminal 100 will be described in detail later.

The information processing server 200 may be a computer included in a cloud computing system or a computer operating alone without depending on other apparatuses. The information processing server 200 acquires training data with reliability from each medical institution terminal 100 and sets a weight to the acquired training data with reliability. In addition, the information processing server 200 performs learning on the basis of weighting data of training data to generate a learned model. Functions of the information processing server 200 will be described in detail later.

Next, functions of the medical institution terminal 100 will be described in detail. In FIG. 1, the medical institution terminal 100 includes, for example, a communication interface 110, an input interface 120, a display 130, a processing circuit 140, and a memory 150. The input interface 120 is an example of an "input." The display 130 is an example of a "display." The memory 150 is an example of a "storage."

The communication interface 110 includes a communication interface, for example, a network interface card (NIC) or the like. The communication interface 110 communicates with the information processing server 200 through the network NW and transmits the training data with reliability to the information processing server 200. In addition, the communication interface 110 may perform communication with other external devices connected through the network NW under the control of the processing circuit 140.

The input interface 120 receives various input operations from an operator such as a doctor, converts the received input operations into electrical signals and outputs the electrical signals to the processing circuit 140. For example, the input interface 120 may be realized by a mouse, a keyboard, a trackball, a switch, a button, a joystick, a touch panel, or the like. In addition, the input interface 120 may be realized by, for example, a user interface which receives audio input, such as a microphone. When the input interface 120 is a touch panel, the display 130 which will be described later may be integrated with the input interface 120.

The display 130 displays various types of information. For example, the display 130 may display an image generated by the processing circuit 140 or a graphical user interface (GUI) or the like for receiving various input operations from an operator. For example, the display 130 may be a liquid crystal display (LCD), a cathode ray tube (CRT) display, an organic electroluminescence (EL) display, or the like.

The processing circuit 140 has, for example, a training data creation function 142 and a reliability setting function 144. The processing circuit 140 realizes these functions, for example, by a hardware processor executing a program (a tool for creating training data with reliability) stored in the memory (storage circuit) 150.

The hardware processor is, for example, a circuitry such as a central processing unit (CPU), a graphics processing unit (GPU), an application specific integrated circuit (ASIC), and a programmable logic device (e.g., a simple programmable logic device (SPLD)), a complex programmable logic device (CPLD) or a field programmable gate array (FPGA)). A program may be directly incorporated into the circuit of the hardware processor instead of being stored in the memory 150. In this case, the hardware processor realizes the function by reading and executing the program incorporated into the circuit. The aforementioned program may be stored in the memory 150 in advance or stored in a non-transitory storage medium such as a DVD or a CD-ROM and installed in the memory 150 from the non-transitory storage medium by mounting the non-transitory storage medium in a drive device (not shown) of the medical institution terminal 100. The hardware processor is not limited to being configured as a single circuit and may be configured as a single hardware processor according to a combination of a plurality of independent circuits to realize each function. In addition, a plurality of components may be integrated into one hardware processor to realize each function. In the first embodiment, the training data creation function 142 is an example of an "acquirer." The reliability setting function 144 is an example of a "reliability setter."

The memory 150 is realized, for example, by a semiconductor memory element such as a random access memory (RAM) or a flash memory, a hard disc, an optical disc or the like. These storage media including a non-transitory storage medium may be realized by other storage devices connected through the network NW such as a network attached storage (NAS) and an external storage server device. In addition, the memory 150 may include a transitory storage medium such as a read only memory (ROM) or a register. The memory 150 stores, for example, a medical image database (DB) 152, a doctor information DB 154, training data 156 with reliability, and other types of information. The medical image DB 152 is a database in which, for example, one or more medical images acquired from a medical image generation apparatus installed in a medical facility in which the medical institution terminal 100 is provided or external devices connected to the network NW are stored. In addition, information about medical images stored in the medical image DB 152 may be associated with the medical images.

Information about a medical image includes a medical image ID that is identification information of the medical image, an image format, a resolution, presence or absence of artifacts, a signal-to-noise ratio (SNR) difference, other photographing conditions of the medical image, and the like. The doctor information DB 154 is, for example, information about doctors belonging to the medical institution terminal 100. The training data 156 with reliability is, for example, data obtained by setting reliability to training data. The training data DB 154 and the training data 156 with reliability will be described in detail later.

For example, the training data creation function 142 may generate training data with respect to a medical image on the basis of an input operation received through the input interface 120 in a state in which an input screen including the medical image is displayed on the display 130. Specifically, the training data creation function 142 displays each medical image or every related medical image included in the medical image DB 152 on the display 130 and receives set of labels through the input interface 120. A label includes, for example, at least one indication of the presence or absence of a lesion for a medical image, identification of a lesion type, and designation of a specific region such as a region of interest (ROI). In addition, a label may include identification of a portion of a test object (e.g., a human body) with respect to a medical image, presence or absence of a disease of the portion, designation of a diseased region (e.g., fibrillogenesis of the lung, a solitary pulmonary nodule, or a region of brain tumor) and the like, a numerical value of seriousness of a disease (e.g., a fatty liver level), and the like.

Figures 2, 3:
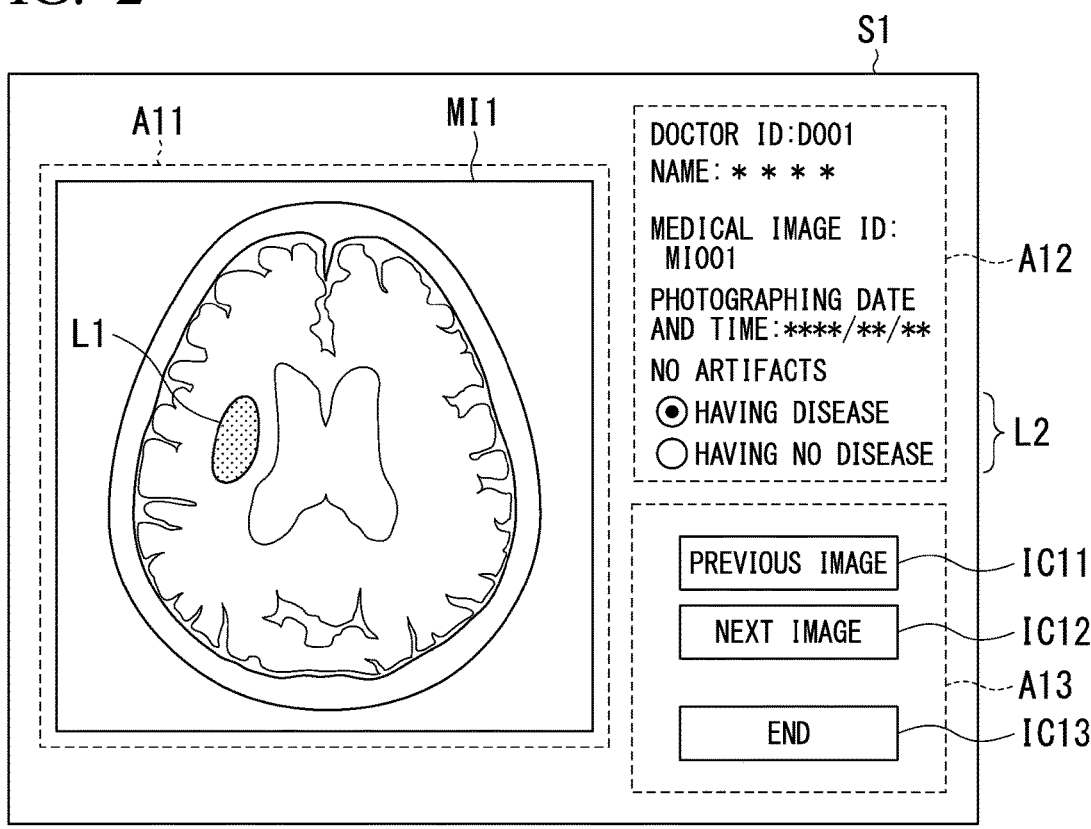
FIG. 2 is a diagram showing an example of an image in which a label is set to a medical image of the first embodiment.
FIG. 3 is a diagram showing an example of details of a medical information DB of the first embodiment.

FIG. 2 is a diagram showing an example of an image S1 in which a label is set to a medical image of the first embodiment. The layout and display details of each item in the image S1 shown in FIG. 2 are not limited thereto. The same applies to other images described below. The image S1 includes, for example, a medical image display area A11, a text information display area A12 and a GUI switch display area A13. A medical image MI1 included in the medical image DB 152 is displayed in the medical image display area A11. In the example of FIG. 2, a CT image of a brain is shown as the medical image MI1. In addition, the medical image display area A11 may include label information L1 about an ROI input by an operator (training data creator) through the input interface 120 with respect to a portion included in the medical image MI1.

The text information display area A12 includes, for example, information about a doctor, information about a medical image, and information about a label set for the medical image MI1. The information about a doctor includes identification information (e.g., login ID) input when the doctor logs in to the medical institution terminal 100, and identification information (e.g., a doctor ID) of an operator which is input when the training data creation function 142 starts. In addition, the information about a doctor may include information acquired from the doctor information DB 154 through the training data creation function 142.

FIG. 3 is a diagram showing an example of details of the doctor information DB 154 of the first embodiment. In the doctor information DB 154, information on items such as "name," "age," "number of years of experience," "technical score," "qualification" and "attendance information" is associated with "doctor ID" that is identification information for identifying a doctor. The "number of years of experience" includes, for example, the number of years of experience of treatment and medical procedures performed as a doctor. The "number of years of experience" may be the number of years of experience in each medical field. Further, the "number of years of experience" may be the number of cases diagnosed by the doctor.

The "technical score" is, for example, information about a technical level with respect to training data creation. For example, the "technical score" may be a technical level based on a cumulative number of creations of training data in the past or a technical level derived on the basis of a difference between a label set to a medical image having a correct answer label in advance without teaching the correct answer and the correct answer level. A label difference is, for example, an error of a label set to a medical image and an ROI position difference, presence or absence of a disease, or a difference between disease details. In addition, the "technical score" may include the number of times of creation of training data about the same field (case), for example. Further, the "technical score" may be allocated for each diagnosis field and each organ or legion type set through training data.

The "qualification" includes, for example, information such as qualifications and results possessed by the doctor with respect to a medical field. In addition, the "qualification" may be qualification information for each organ or legion type set through training data. The "attendance information" includes, for example, information about working hours and days off in a predetermined period (e.g., about one week to one month) for each doctor identified through identification information, and the like. For example, the "attendance information" may be acquired from an attendance management system in a medical facility in which the medical institution terminal 100 is provided, an external device connected through the network NW, or the like.

The training data creation function 142 refers to "doctor IDs" of the doctor information DB 154, for example, on the basis of a login ID or a doctor ID input from an operator, acquires information about a doctor associated with a matching doctor ID and displays the information in the text information display area A12. In the example of FIG. 2, a doctor ID and a name acquired from the doctor information DB are displayed in the text information display area A12. With respect to information about a doctor displayed in the text information display area A12, the same information is displayed until set of labels for a series of medical images through the training data creation function 142 is completed, that is, while the training data creation function 142 is continuously executed.

In addition, information about a medical image may be information acquired from the medical image DB 152 or information obtained by analyzing the medical image through the training data creation function 142. In the example of FIG. 2, a medical image ID and presence or absence of artifacts are displayed as information about a medical image in the text information display area A12. Further, in the example of FIG. 2, information about the presence or absence of a disease with respect to the medical image MI1 is displayed as information about a label input by an operator through the input interface 120 in the text information display area A12.

The GUI switch display area A13 includes, for example, an icon through which medical images displayed in the medical image display area A11 are switched, an icon through which the training data creation function 142 is ended, and the like. In the example of FIG. 2, an icon IC11 for displaying a medical image stored before a currently displayed medical image from among a plurality of medical images stored in the medical image DB 152, an icon IC12 for displaying a medical image stored after the currently displayed medical image, and an icon IC13 for ending execution of the training data creation function 142 are displayed in the GUI switch display area A13.

The training data creation function 142 generates the above-described image S1, displays the image S1 on the display 130 and receives input of a label from an operator. In addition, when an operation of any of the icons IC11 to IC13 displayed in the GUI switch display area A13 is received, the training data creation function 142 associates the received information with a medical image and stores the information associated with the medical image in the training data 156 with reliability. Further, when an operation of any of the icons IC11 to IC13 displayed in the GUI switch display area A13 is received, the reliability setting function 144 is executed.

The reliability setting function 144 generates an image S2 corresponding to an inquiry screen for setting reliability of training data in which a label has been set to a medical image and displays an input screen including the generated image S2 on the display 130. In this case, the reliability setting function 144 may end display of the image S1 and display the image S2 or display the image S2 overlaid on (the front face of) the displayed image S1.

Figure 4:
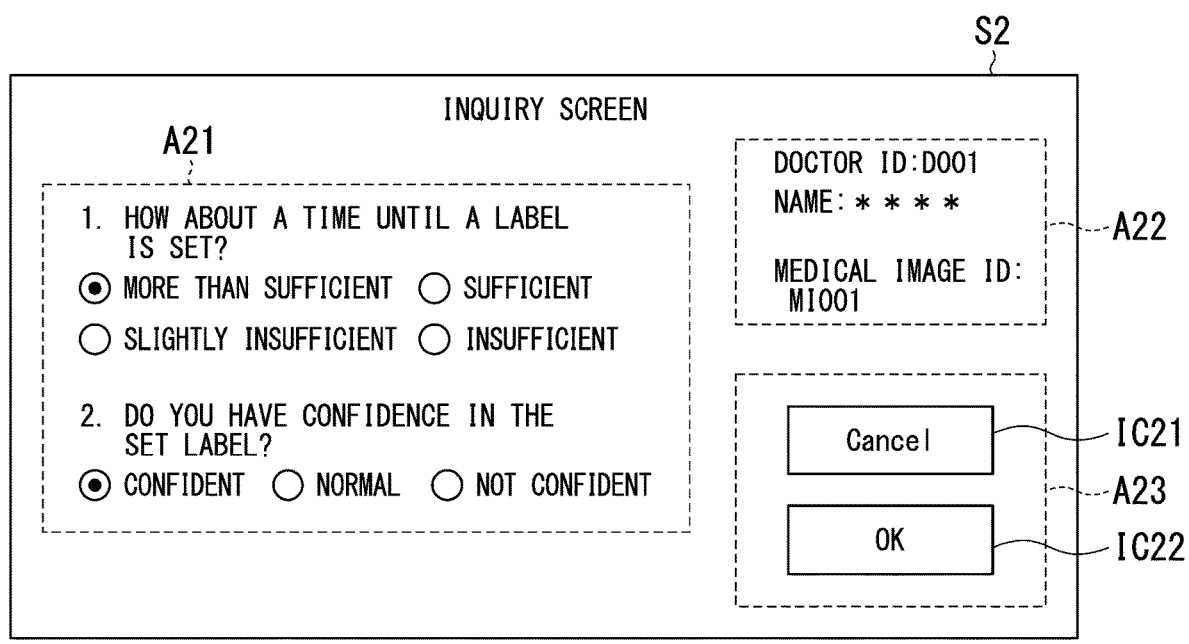
FIG. 4 is a diagram showing an example of an image of the first embodiment.

FIG. 4 is a diagram showing an example of the image S2 of the first embodiment. The image S2 includes, for example, a reply input area A21, a text display area A22, and a GUI switch display area A23. The reply input area A21 includes, for example, inquiry details with respect to a doctor or the like, and selection item information for allowing the doctor to select at least one of a plurality of reply items for the inquiry details. In the example of FIG. 4, a radio button through which one of a plurality of choices defined in advance for an inquiry is selected is illustrated. Meanwhile, the selection item information may include check boxes through which a plurality of items can be selected from a plurality of choices, a text box through which text can be input, or the like instead of (or in addition to) the aforementioned radio buttons.

For example, information that is the same as or simplified from information of the image S1 displayed in the text display area A12 may be displayed in the text display area A22. In the example of FIG. 4, a doctor ID, a name and a medical image ID are displayed. In addition, the GUI switch display area A23 includes, for example, an icon IC21 for displaying the image S1 without confirming details indicated through the inquiry screen and an icon IC22 for ending a reply to an inquiry and executing processing associated with any of the icons A11 to A13.

In the example of FIG. 4, inquiry information about a time until a label is set (hereinafter referred to as "first inquiry information") and inquiry information about a confidence degree with respect to a set label (hereinafter referred to as "second inquiry information") are displayed in the reply input area A21. The first inquiry information displays choices of "more than sufficient," "sufficient," "slightly insufficient" and "insufficient" and the second inquiry information displays choices of "confident," "normal" and "not confident." The reliability setting function 144 receives one of those choices from an operator. The reliability setting function 144 can acquire awareness information of a training data creator by receiving a reply to the inquiry of the image S2. When a plurality of labels has been set to medical images, the above-described inquiry may be performed for each label or collectively performed for each medical image. In addition, the reliability setting function 144 associates information acquired through the inquiry screen of the image S2 with a medical image, stores the information associated with the medical image in the training data 156 with reliability and ends display of the image S2 when an operation of selecting the icon IC22 is received.

FIG. 5 is a diagram showing an example of details of the training data 156 with reliability of the first embodiment.

In the training data 156 with reliability, information of items such as a "medical image," "label information," "operation situations" and "creator information" is associated with a "training data ID" that is identification information of training data. Some or all of the "operation situations" and "creator information" are an example of "reliability information." The label information includes, for example, information about labels (e.g., labels L1 and L2 shown in FIG. 2) input with respect to the aforementioned image S1.

The "operation situations" include, for example, information associated with items such as "time required for creation," "confidence degree," "freshness degree" and "quality." The "time required for creation" is, for example, an index indicating a degree of awareness with respect to deficiency and excess of a time required for creation associated with choices of reply information for the first inquiry information of the image S2. The reliability setting function 144 sets a confidence degree based on a reply result for the first inquiry information. For example, when an operator is aware that the time for set a label is sufficient, the reliability setting function 144 may set a higher confidence degree than that when the operator is aware that the time is not sufficient. For example, the "time required for creation" may be an index value based on a time from display of a medical image to end of the display. The reliability setting function 144 measures a time from when a medical image that is a target to be set a label is displayed to when the next medical image is displayed or until the training data creation function 142 ends, increases an index value as the measured time increases and stores the index value in the item of the time required for creation.

The "confidence degree" is a quality of subjective training data of a training data creator (reliability of trusting that the training data is correct). The "confidence degree" is set based on a reply result for the second inquiry information of the image S2. In this case, the reliability setting function 144 increases the value of a confidence degree to higher than that in the case in the case of a reply representing normal confidence or lack of confidence when a reply represents confidence and increases the value of the confidence degree to higher than that in the case of a reply representing lack of confidence when the reply represents normal confidence.

The "freshness degree" is for example, a medical image creation time or a training data creation time. A creation time includes date and time information. In addition, the "freshness degree" may be the number of days that have elapsed since a creation time. The "quality" is, for example, information about a quality of a medical image and includes an image format, presence or absence of artifacts, an SNR difference, other medical image photographing conditions, and the like.

The "creator information" includes, for example, information of items such as "number of years of experience," "technical score," "qualification" and "busyness degree." The "number of years of experience," "technical score" and "qualification" are information acquired from the doctor information DB 154 on the basis of a doctor ID. The "busyness degree" is an index value indicating a degree of busyness or fatigue which is estimated on the basis of attendance information included in doctor information. The reliability setting function 144 sets the value of a busyness degree such that the value increases as a time for which training data is continuously created increases. In addition, the reliability setting function 144 may make an inquiry about the busyness of an operator and store a busyness degree based on a result of a reply thereto. Further, the reliability setting function 144 may acquire bio-information (e.g., a pulse and brainwaves) during creation which is obtained from a biosensor or the like attached to a training data creator through the network NW, estimate a tension state, a load state or the like from the acquired bio-information and estimate a busyness degree on the basis of the estimation result. In this case, the reliability setting function 144 sets the value of the busyness degree such that the value increases as the tension state or load state is high or a period in which the tension state or load state is equal to or greater than a threshold value increases.

In addition, the reliability setting function 144 outputs training data with reliability stored in the memory 150 to the information processing server 200 through the network NW.

Next, functions of the information processing server 200 will be described in detail. Referring back to FIG. 1, the information processing server 200 includes, for example, a communication interface 210, an input interface 220, a display 230, a processing circuit 240 and a memory 250. The input interface 220 is an example of an "input." The display 230 is an example of a "display." The memory 250 is an example of a "storage."

The communication interface 210 includes, for example, a communication interface such as an NIC. The communication interface 210 communicates with the medical institution terminal 100 through the network NW and receives the training data 156 with reliability from the medical institution terminal 100.

The input interface 220 receives various input operations from an operator, converts the received input operations into electrical signals and outputs the electrical signal to the processing circuit 240. For example, the input interface 220 may be realized by a mouse, a keyboard, a trackball, a switch, a button, a joystick, a touch panel, or the like. In addition, the input interface 220 may be realized by, for example, a user interface which receives audio input, such as a microphone. When the input interface 220 is a touch panel, the display 230 which will be described later may be integrated with the input interface 220.

The display 230 displays various types of information. For example, the display 230 may display an image generated by the processing circuit 240 or a GUI or the like for receiving various input operations from an operator. For example, the display 230 may be an LCD, a CRT display, an organic EL display, or the like.

The processing circuit 240 has, for example, an acquisition function 242, a weighting function 244 and a learning function 246. For example, the processing circuit 240 may realize these functions by a hardware processor executing a program stored in the memory (storage circuit) 250.

The hardware processor is, for example, circuitry such as a CPU, a GPU, an application specific integrated circuit, a programmable logic device, or a field programmable gate array. A program may be directly incorporated into the circuit of the hardware processor instead of being stored in the memory 250. In this case, the hardware processor realizes the function by reading and executing the program incorporated into the circuit. The aforementioned program may be stored in the memory 250 in advance or stored in a non-transitory storage medium such as a DVD or a CD-ROM and installed in the memory 250 from the non-transitory storage medium by mounting the non-transitory storage medium in a drive device (not shown) of the information processing server 200. The hardware processor it not limited to being configured as a single circuit and may be configured as a single hardware processor according to a combination of a plurality of independent circuits to realize each function. In addition, a plurality of components may be integrated into one hardware processor to realize each function. The weighting function 244 and the learning function 246 are an example of a "learner."

The memory 250 is realized, for example, by a semiconductor memory element such as a RAM or a flash memory, a hard disk, an optical disc or the like. These storage media including a non-transitory storage medium may be realized by other storage devices connected through the network NW such as a NAS and an external storage server device. In addition, the memory 250 may include a transitory storage medium such as a ROM or a register. The memory 250 stores, for example, training data 252 with reliability, a weighting table 254, weighted training data 256, a learned model 258, and other types of information. The weighting table 254 and the weighted training data 256 will be described in detail later.

The acquisition function 242 acquires the training data 252 with reliability from the medical institution terminal 100 and stores the acquired training data 252 with in the memory 250. The training data 252 with reliability may be the same item as the training data 156 with reliability or a medical institution terminal ID that is identification information of the medical institution terminal 100 may be attached thereto in order to identify the medical institution terminal 100 from which the training data with reliability has been acquired.

The weighting function 244 sets a normalized weight to reliability information (operation situations and operator information) included in the training data 252 with reliability on the basis of training data 252 with reliability and the weighting table 254. For example, the weighting function 244 sets a weighting score normalized in a predetermined range of numerical values of 1 to 5 or the like to each item included in the reliability information of the training data 252 with reliability on the basis of details of each item.

FIG. 6 is a diagram showing an example of details of the weighting table 254 of the first embodiment. The weighting table 254 shown in FIG. 6 is a table in which a "weighting score" is associated with a "time required for creation." The "time required for creation" is different for careers or proficiencies of training data creators, and there are cases in which training data with high quality can be created even within a short time. Variation in the quality of training data occurs, for example, due to a relationship between an operation time and a creator's skill. That is, when an operation is performed under a situation in which a time is not set depending on the creator's skill, a possibility of generation of a mistake or error such as incorrect details of a label to be set increases and deterioration of the quality of training data may be caused. Accordingly, the weighting function 244 sets a weighting score based on awareness information of a creator with respect to a time required for creation using the weighting table 254 in which weighting scores depending on degrees perceived to be sufficient in time have been set.

In addition, the weighting function 244 may set a weighting score on the basis of a difference between a preset optimal time required for creation and a time required for creation (i.e., a degree of deviation from the optimal time required for creation) instead of (or in addition to) setting a weighting score based on awareness information of a creator with respect to the time required for creation. The optimal time required for creation is, for example, a value determined by attribute information of a creator, and a short time is set for a creator having high proficiency or much experience, and in contrast, a long time is set for an inexperienced creator. Accordingly, when a time required for creation is excessively long even though the creator is experienced or a time required for creation is excessively short even though the creator is inexperienced, weight allocation can be performed such that reliability decreases.

In the first embodiment, the same weighting table as that of FIG. 6 is also provided for items other than the "time required for creation" ("confidence degree," "freshness degree," "quality," "number of years of experience," "technical score," "qualification" and "busyness degree"). The weighting function 244 sets a weight score to each item using a weighting table corresponding to each item. Here, the meaning of weighting each of the aforementioned items other than the "time required for creation" will be described.

The "confidence degree" is a value that varies according to various situations encountered in creation of training data, such as variations in the quality of training data due to conditions of a training data creator or cases in which the creator is confused with respect to a case that is very difficult to determine or, on the other hand, confusion does not occur in creation of training data. The weighting function 244 can associate the value of training data with a state of the creator during creation by setting a weight score based on a subjective index value of the creator and can use the value of the training data for determination of the quality of the training data, and the like.

With respect to the "freshness degree," a medical determination such as the diagnosis of disease and treatment options is not unchangeable and the determination also changes according to legislation, amendment of guidelines, medical progress, and the like over time. Accordingly, occurrence of a situation in which training data with different answers may be present due to a difference between training data creation times is also conceivable. Therefore, the weighting function 244 sets a weight score depending on a creation time and the like. Specifically, the weighting function 244 sets weight scores such that reliability increases as a creation time of a medical image or training data acquired through the acquisition function 242 becomes later. Accordingly, training data that is correct at this point in time can be acquired with high efficiency and training data with stabilized quality is acquired.

With respect to the "quality," variations in the quality of training data are expected to occur for training data due to the presence or absence of artifacts, SNR difference, and different image conditions. Accordingly, the weighting function 244 can select learning data in optimal image conditions required for learning with high efficiency by setting a weight score to image quality.

With respect to the "number of years of experience," it is conceivable that determination of a disease or a lesion varies and the quality of training data changes depending on the number of years of experience of a training data creator. For example, although there is a textbook definition of a boundary between a lesion and a normal portion, in general, determination of a lesion part is based on the experience of a creator in cases in which a disease is in an initial stage, cases in which a disease is minimal, and cases in which a disease is complex and complicated and the boundary thereof is not distinct. Accordingly, the weighting function 244 can reflect training data quality differences due to experience of doctors in training data by setting a weight score to the number of years of experience.

The "technical score" is an index value for measurement of the ability (skill) of a creator who creates training data and is different for doctors. Accordingly, the weighting function 244 can determine the quality of training data by a technical score of a creator by setting a weight score to the technical score.

With respect to the "qualification," there are cases in which a doctor has expertise according to his/her education and experience and holds qualifications indicating that the doctor has a specific technique in the special field. For example, a conference of each special field acknowledges and grants such qualifications and the qualifications are classified for registered medical practitioners, certified physicians, medical specialists, medical instructors, and the like in many cases in Japan. Overseas, although there are different systems in each country, the American Board of Medical Specialty (ABMS) and the British Postgraduate Medical Education and Training Board (PMETB) perform evaluation and acknowledgement of medical specialists as the similar qualifications. Such information on qualifications of doctors is information representing skills of doctors evaluated by public institutions and academic societies. Accordingly, the weighting function 244 can ascertain the quality of training data more accurately by setting a weight score to qualifications.

The "busyness degree" is an index value of a condition of a doctor. A large number of days of consecutive work or long working hours may cause lack of the accuracy of determination of label set. Accordingly, the weighting function 244 can ascertain the quality of training data more accurately by setting a weight score to a busyness degree.

The weighting function 244 may set a weight score to a result of combination of a plurality of items as well as weighting each of the aforementioned items. FIG. 7 is a diagram showing an example of a weighting table 254a for a plurality of items of the first embodiment. In the weighting table 254a, a "weight score" is associated with a "time required for creation" and a "number of years of experience." For example, even when a time required for creation is sufficient, it is estimated that there is a possibility of unlabeled portion or wrong determination due to lack of experience or the like, for example, using the weighting table 254a as shown in FIG. 7 when the number of years of experience is few. Accordingly, the weighting function 244 can set a weight score such that the value decreases as the number of years of experience decreases using the weighting table 254a even when a time required for creation is sufficient. In this manner, it is possible to set a more suitable weight by setting a weight score using a table for combining a plurality of items and setting a weight score thereto.

FIG. 8 is a diagram showing an example of details of the weighted training data 256 of the first embodiment. In the weighted training data 256, for example, information of items such as "medical image," "label information," "operation situation score" and "creator information score" may be associated with "training data ID." The "operation situation score" includes, for example, information of items such as "time required for creation," "confidence degree," "freshness degree" and "quality." The "creator information score" includes, for example, information of items such as "number of years of experience," "technical score," "qualification" and "busyness degree."

The weighted training data 256 may include, for example, a sum score or an average score of one or both of "operation situation scores" and "creator information scores" derived by the weighting function 244.

Referring back to FIG. 1, the learning function 246 generates a learned model 258 having a medical image as an input and label information as an output for the weighted training data 256 stored in the memory using a predetermined machine learning algorithm.

The learning function 246 includes, for example, a deep neural network (DNN) using a convolutional neural network (CNN). For example, the learning function 246 causes the DNN to learn a neural network through a machine learning algorithm such as error back propagation. For example, the learning function 246 may perform processing of constructing a function f(w, d) for an input d using a parameter w, defining a loss L(t, f(w, d)) for training data t and minimizing the loss in supervised learning in machine learning. In addition, the learning function 246 performs learning by calculating the loss L(t, f(w, d)) for sets (di, ti) of various inputs d and training data t and determining the parameter w such that the loss L(t, f(w, d)) decreases for each set.

For example, when a plurality of pieces of training data are represented by T={t1, t2, . . . , tn} and a plurality of input medical images are represented as D={d1, d2, . . . , dn}, the learning function 246 adjusts the parameter w such that the training data t becomes close to the output f(w, d) of the function using a loss function LOSS (expression (1)) below.

$$\text{LOSS}(T, D) = \sum_{i=1}^{n} \{f(ti) - f(w, di)\} \quad (1)$$

In addition, when the above-described learning is performed, the learning function 246 adjusts a degree of change of a coefficient (e.g., the aforementioned parameter w) between nodes of the neural network on the basis of weight scores of weighted training data 256. Further, when a learning model is corrected such that a difference (loss) between correct-answer data and data of the learning model becomes 0, the learning function 246 may adjust an amount by which the difference is reflected in the learning model using weight scores. In this manner, it is possible to improve the quality of the learned model 258 by generating the learned model 258 on the basis of the aforementioned weight scores.

The learning function 246 stores the generated learned model 258 in the memory 250. In addition, the stored learned model 258 may be transmitted to the medical institution terminal 100 through the network NW. In this case, the processing circuit 140 of the medical institution terminal 100 determines presence or absence of a label and sets a label for an input of a medical image using the learned model 258.

Figure 9:
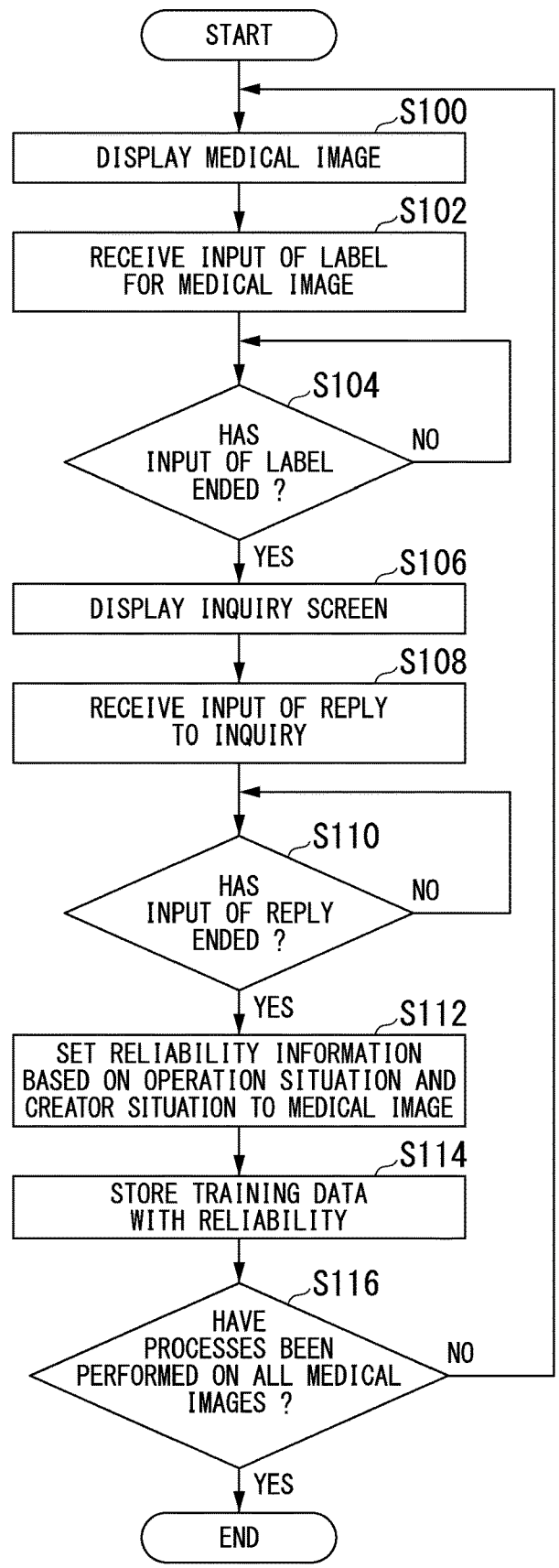
FIG. 9 is a flowchart showing a flow of a series of processes of a processing circuit of a medical institution terminal of the first embodiment.

Next, a flow of a series of processes of the processing circuit 140 of the medical institution terminal 100 in the first embodiment will be described using the drawing. FIG. 9 is a flowchart showing the flow of a series of processes of the processing circuit 140 of the medical institution terminal 100 of the first embodiment. The processes of FIG. 9 may be repeatedly performed at a predetermined interval or timing. In the example of FIG. 9, the training data creation function 142 displays a medical image stored in the medical image DB 152 on the display 130 (step S100). Next, the training data creation function 142 receives an input of a label for the medical image (step S102). Then, the training data creation function 142 determines whether the input of the label for the medical image has ended (step S104). In the process of step S104, for example, the training data creation function 142 may determine that the input of the label has ended when any of the icons IC11 to IC13 included in the aforementioned image S1 is selected or determine that the input of the label has ended when a state in which an input is not received from when the image S1 is displayed continues for a predetermined time or longer. Further, the training data creation function 142 waits until it is determined that the input of the label has ended when the above-described conditions are not satisfied.

When it is determined that the input of the label has ended, the reliability setting function 144 displays the inquiry image S2 on the display 130 (step S106). Next, the reliability setting function 144 receives an input of a reply to an inquiry (step S108). Then, the reliability setting function 144 determines whether the input of the reply to the inquiry has ended (step S110). In the process of step S110, the reliability setting function 144 may determine that the input of the reply has ended when the icon IC22 included in the aforementioned image S2 is selected or determine that the input of the reply has ended when a state in which an input is not received from when the image S2 is displayed continues for a predetermined time or longer, for example. In addition, the reliability setting function 144 waits until it is determined that the input of the reply has ended when the above-described conditions are not satisfied.

When it is determined that the input of the reply has ended, the reliability setting function 144 sets reliability information based on an operation situation and a creator situation to the medical image (step S112) and stores training data 154 with reliability to which the reliability information has been set in the memory 150 (step S114). Next, the processing circuit 140 determines whether the processes have been performed on all medical images that are processing targets (step S116). When it is determined that the processes have not been performed on all medical images that are processing targets, the flow retunes to step S100 and displays the next image. Further, when it is determined that the processes have been performed on all medical images, this flowchart ends.

Next, a flow of a series of processes of the processing circuit 240 of the information processing server 200 in the first embodiment will be described using the drawing.

Figure 10:
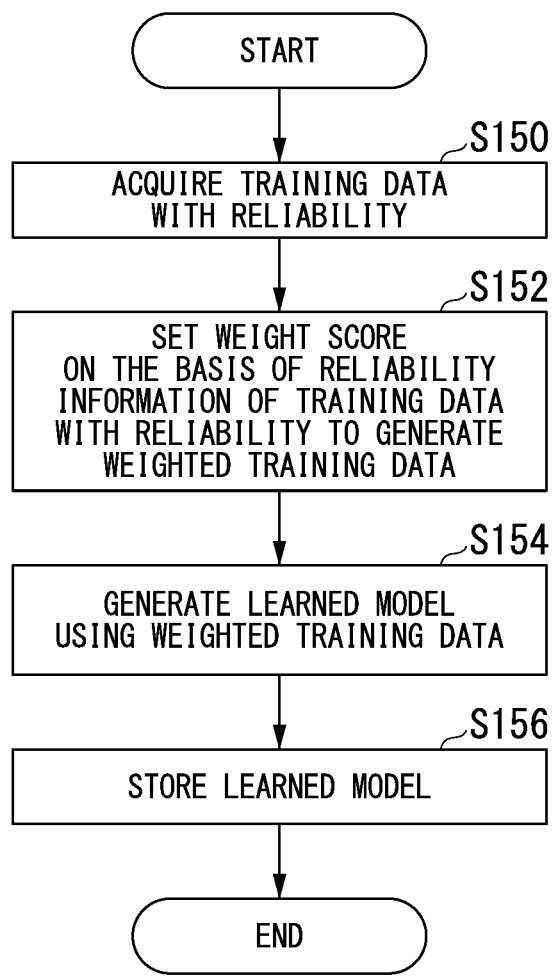
FIG. 10 is a flowchart showing a flow of a series of processes of a processing circuit of an information processing server of the first embodiment.

FIG. 10 is a flowchart showing the flow of a series of processes of the processing circuit 240 of the information processing server 200 of the first embodiment. The processes of FIG. 10 may be repeatedly performed at a predetermined interval or timing. In the example of FIG. 10, the acquisition function 242 acquires training data 252 with reliability from each medical institution terminal 100 (step S150). Next, the weighting function 244 sets a weight score to a label set to a medical image on the basis of reliability information of the acquired training data with reliability to generate weighted training data (step S152).

Next, the learning function 246 generates a learned model 258 which outputs label information for an input of a medical image using the weighted training data (step S154) and stores the generated learned model 258 in the memory 250 (step S156). Meanwhile, the generated learned model 258 may be transmitted to the medical institution terminal 100 through the network NW in the process of step S156.

According to the above-described first embodiment, it is possible to clarify the quality of training data even in the case of limited training data with unstable quality in the medical field. Further, it is possible to obtain stabilized learning results to which the quality of training data has been added according to the first embodiment.

Second Embodiment

Hereinafter, a second embodiment will be described. The second embodiment differs from the above-described first embodiment in that a medical processing apparatus includes the reliability setting function. Accordingly, the following description will focus on differences from the first embodiment and the same parts as those of the first embodiment will be attached the same names and signs and detailed description thereof will be omitted.

Figure 11:
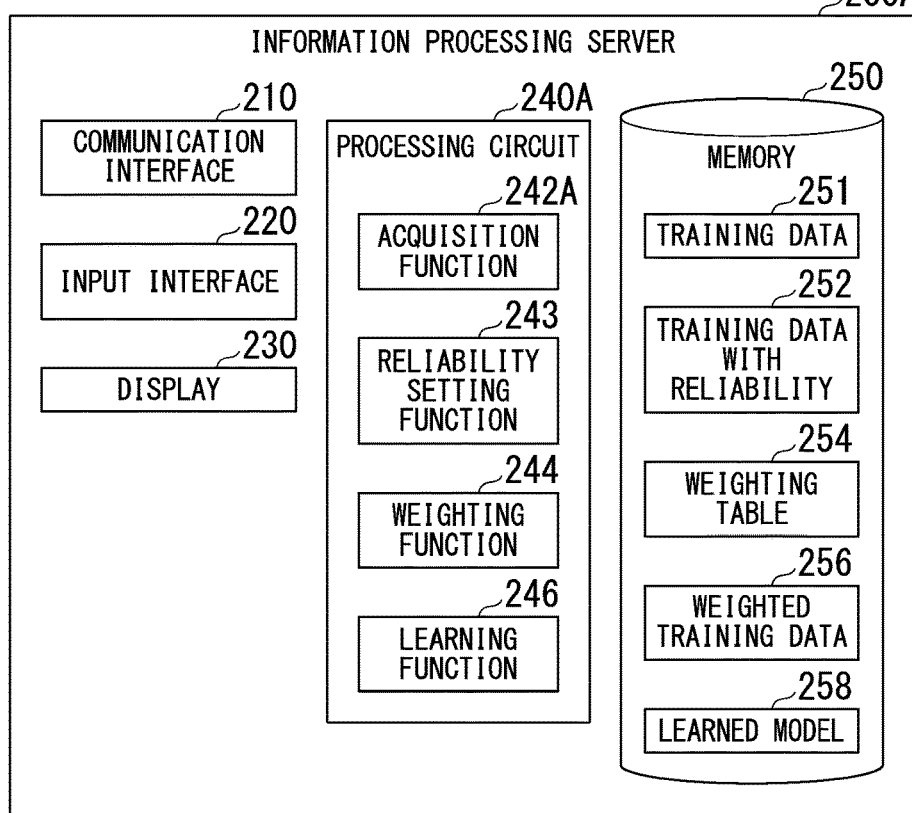
FIG. 11 is a diagram showing an example of a medical image processing system including an information processing server of a second embodiment.

FIG. 11 is a diagram showing an example of a medical image processing system 2 including an information processing server 200A of the second embodiment. The medical image processing system 2 includes, for example, one or more medical institution terminals 100A-1 to 100A-n and an information processing server 200A. In the second embodiment, the information processing server 200A is an example of a "medical image processing apparatus."

The medical institution terminal 100A includes, for example, a communication interface 110, an input interface 120, a display 130, a processing circuit 140A, and a memory 150A. The medical institution terminal 100A includes the processing circuit 140A and the memory 150A instead of the processing circuit 140 and the memory 150 as compared to the configuration of the medical institution terminal 100 of the first embodiment. The processing circuit 140A includes, for example, a training data creation function 142A. The memory 150A includes a medical image DB 152, a doctor information DR 154, and training data 158.

Figures 12, 13:
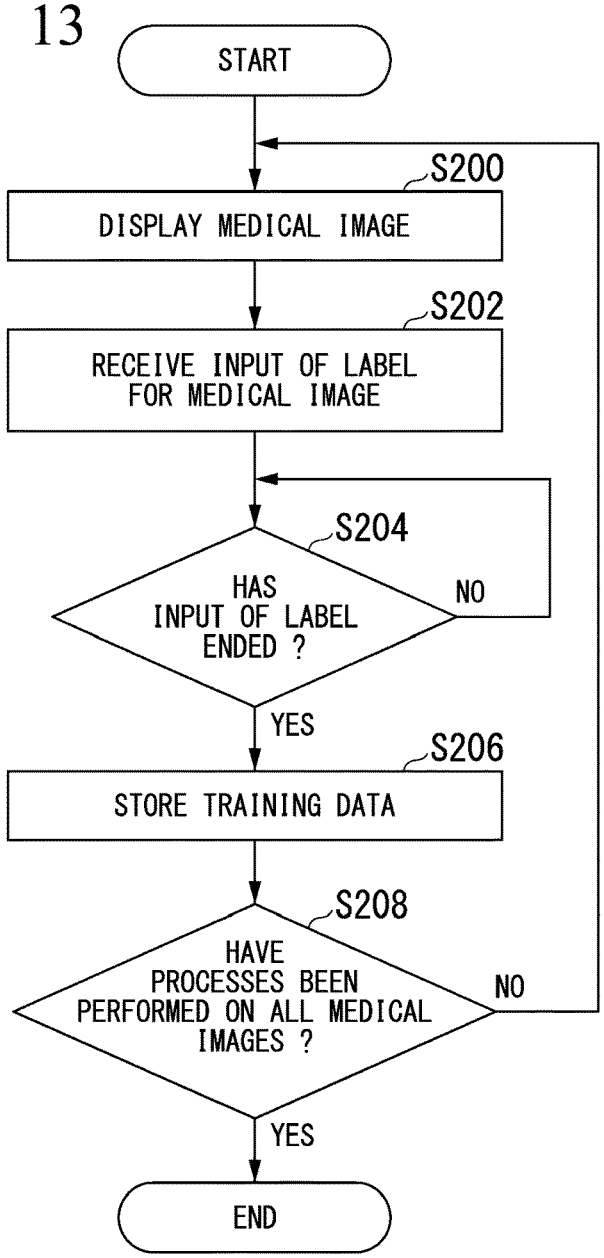
FIG. 12 is a diagram showing an example of details of training data of the second embodiment.
FIG. 13 is a flowchart showing a flow of a series of processes of a processing circuit of a medical institution terminal of the second embodiment.

FIG. 12 is a diagram showing an example of details of the training data 158 of the second embodiment. In the training data 158, for example, information of items such as "medical image," "label information" and "supplementary information" may be associated with "training data ID." The "supplementary information" includes, for example, information of items such as "time required for creation," "freshness degree," "quality" and "doctor information." The time required for creation included in the "supplementary information" is not subjective information of a creator and is a time required until a label is set, and specifically, is a time required from display of a medical image to end of the display. The "doctor information" is, for example, at least one piece of information from among information about doctors which can be acquired from the doctor information DB 154.

The training data creation function 142A receives an input of a label for a medical image displayed in the aforementioned image S1 and stores, in the memory 150A, training data 158 set supplementary information with respect to creation of training data at a time when the input is ended. In addition, the training data creation function 142A transmits the training data 158 to the information processing server 200A when an inquiry is received from the information processing server 200A or at a predetermined timing such as predetermined intervals.

The information processing server 200A includes, for example, a communication interface 210, an input interface 220, a display 230, a processing circuit 240A and a memory 250A. The information processing server 200A includes the processing circuit 240A and the memory 250A instead of the processing circuit 240 and the memory 250 as compared to the configuration of the information processing server 200 of the first embodiment.

The processing circuit 240A includes, for example, an acquisition function 242A, a reliability setting function 243, a weighting function 244 and a learning function 246. The acquisition function 242A acquires training data 158 from the medical institution terminal 100A through the network NW and stores the acquired training data as training data 251 in the memory 250A. The training data 251 may be set a medical institution terminal ID.

The reliability setting function 243 generates training data 252 with reliability on the basis of the training data 251 stored in the memory 250A. Specifically, the reliability setting function 243 generates the aforementioned items "operation situation" and "operator information" on the basis of supplementary information with respect to the training data 158. With respect to information which cannot be acquired from the supplementary information among these items, a value for the item may not be input or a preset value may be input.

In addition, the reliability setting function 243 may display the aforementioned image S1 and image S2 on the display 230 and allow an operator of the information processing server 200A to set label information or reliability information. Training data set reliability is stored in the memory 250A as training data 252 with reliability.

Next, a flow of a series of processes of the processing circuit 140A of the medical institution terminal 100A in the second embodiment will be described using the drawing.

FIG. 13 is a flowchart showing the flow of a series of processes of the processing circuit 140A of the medical institution terminal 100A of the second embodiment. The processes of FIG. 13 may be repeatedly performed at a predetermined interval or timing. In the example of FIG. 13, processes of steps S200 to S204 are the same as the above-described processes of steps S100 to S104 shown in FIG. 9 and thus detailed description thereof will be omitted here.

The training data creation function 142A stores created training data in the memory 150A when it is determined that input of a label has ended in the process of step S204 (step S206). Next, the training data creation function 142A determines whether the processes have been performed on all medical images which are processing targets (step S208). When it is determined that the processes have not been performed on all medical images which are processing targets, the training data creation function 142A returns to step S200 and displays the next image. On the other hand, when it is determined that the processes have been performed on all medical images which are processing targets, the processes of this flowchart end.

Next, a flow of a series of processes of the processing circuit 240A of the information processing server 200A in the second embodiment will be described using the drawing.

Figure 14:
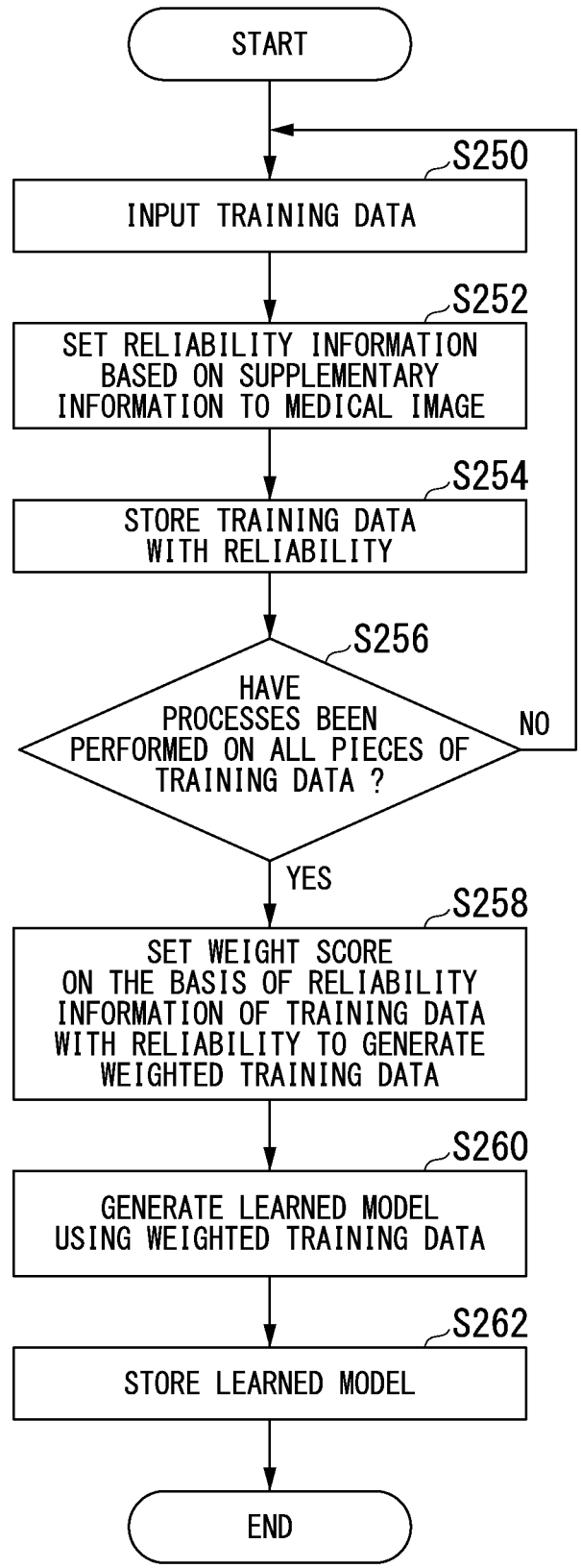
FIG. 14 is a flowchart showing a flow of a series of processes of a processing circuit of an information processing server of the second embodiment.

FIG. 14 is a flowchart showing the flow of a series of processes of the processing circuit 240A of the information processing server 200A of the second embodiment. Processes of steps S258 to S262 in FIG. 14 are the same as the above-described processes of steps S152 to S156 and thus detailed description thereof will be omitted here and description will be made focusing on steps S250 to S256.

The acquisition function 242 acquires training data 252 from each medical institution terminal 100A (step S250). Next, the reliability setting function 243 sets reliability information based on supplementary information of the acquired training data to a medical image (step S252). Then, the reliability setting function 243 stores the training data 252 with reliability to which the reliability information has been set in the memory 250A (step S254). Subsequently, the reliability setting function 243 determines whether the processes have been performed on all pieces of training data which are processing targets (step S256). When it is determined that the processes have not been performed on all pieces of training data which are processing targets, the flow returns to the process of step S250 and receives a record of next training data. On the other hand, when it is determined that the processes have been performed on all pieces of training data which are processing targets, processes after step S256 are performed.

According to the above-described second embodiment, it is possible to reduce loads of the medical institution terminal 100A and loads of a training data creator by setting reliability information in the information processing server 200A in addition to obtaining the same effects as those of the first embodiment.

In general, it is difficult to prepare a sufficient amount of training data because the number of medical images is limited, and when creation of training data is performed manually, the quality of training data may vary in the medical field. In the second embodiment, it is possible to improve the quality of training data even in the case of limited training data with unstable quality. Further, according to the second embodiment, it is possible to obtain stabilized learning results to which the quality of training data has been added.

Third Embodiment

Hereinafter, a third embodiment will be described. The third embodiment differs from the second embodiment in that a medical image processing server has a function of adjusting a weight score or adjusting whether the weight score is included in learned data. Accordingly, the following description will focus on differences from the second embodiment and the same parts as those of the second embodiment will be attached the same names and signs and detailed description thereof will be omitted. In addition, the medical institution terminal 100A in the third embodiment has the same configuration as that of the second embodiment and thus description thereof will be omitted here.

Figure 15:
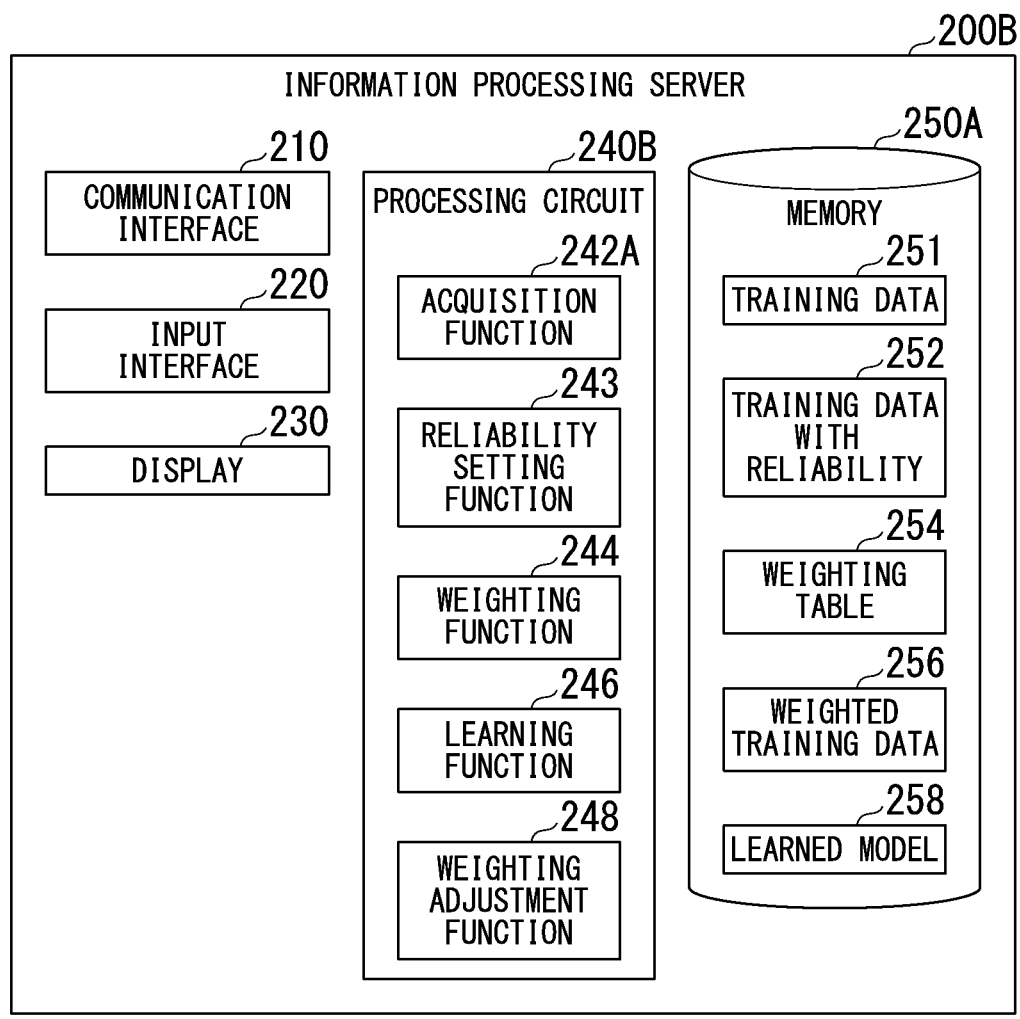
FIG. 15 is a diagram showing an example of a configuration of an information processing server of a third embodiment.

FIG. 15 is a diagram showing an example of a configuration of an information processing server 200B of the third embodiment. In the third embodiment, the information processing server 200B is an example of a "medical image processing apparatus." The information processing server 200B includes, for example, a communication interface 210, an input interface 220, a display 230, a processing circuit 240B and a memory 250A. The information processing server 200B includes the processing circuit 240B instead of the processing circuit 240 as compared to the configuration of the information processing server 200A of the second embodiment.

The processing circuit 240B includes, for example, an acquisition function 242A, a reliability setting function 243, a weighting function 244, and an adjustment function 248. The adjustment function 248 is an example of an "adjuster." The adjustment function 248 adjusts, for example, weight scores included in the weighting table 254 and the weighted training data 256. For example, the adjustment function 248 may generate an image through which information about the weighting table 254 and the weighted training data 256 is displayed on the display and update the weighting table 254 and the weighted training data 256 on the basis of information changed by an operator using the generated image.

In addition, when the weighting table 254 has been updated, the adjustment function 248 causes the weighting function 244 to regenerate the weighted training data 256 using the updated weighting table. Further, when the weighted training data 256 has been updated, the adjustment function 248 may cause the learning function 246 to regenerate the learned model 258 using the updated weighted training data. Accordingly, it is possible to generate the weighted training data 256 and the learned model 258 in response to the state of a more recent medical field.

In addition, when details of a reference have changed due to revision of medical guidelines, and the like, the adjustment function 248 may update an object part of the weighting table 254 on the basis of the changed details. In this case, when a diagnosis guideline corresponding to a label (e.g., the type of a set organ or lesion) included in training data has been updated, for example, the adjustment function 248 may perform adjustment for decreasing a weight score for "freshness degree" of weighted training data older than the guideline update date.

Further, the adjustment function 248 may exclude training data in which values of operation situation scores or creator information scores are equal to or less than a predetermined value from among the weighted training data 256 from inputs of the learning function 246. Accordingly, it is possible to generate the learned model 258 using training data with higher reliability. In addition, it is possible to reduce a time required to generate the learned model 258 because useless training data can be omitted.

Furthermore, the adjustment function 248 may delete training data in which values of operation situation scores or creator information scores are equal to or less than a predetermined value from among the weighted training data 256 from the weighted training data 256. Accordingly, it is possible to reduce a data capacity of the memory 250A.

Next, a flow of a series of processes of the processing circuit 240B of the information processing server 200B in the third embodiment will be described using the drawing.

Figure 16:
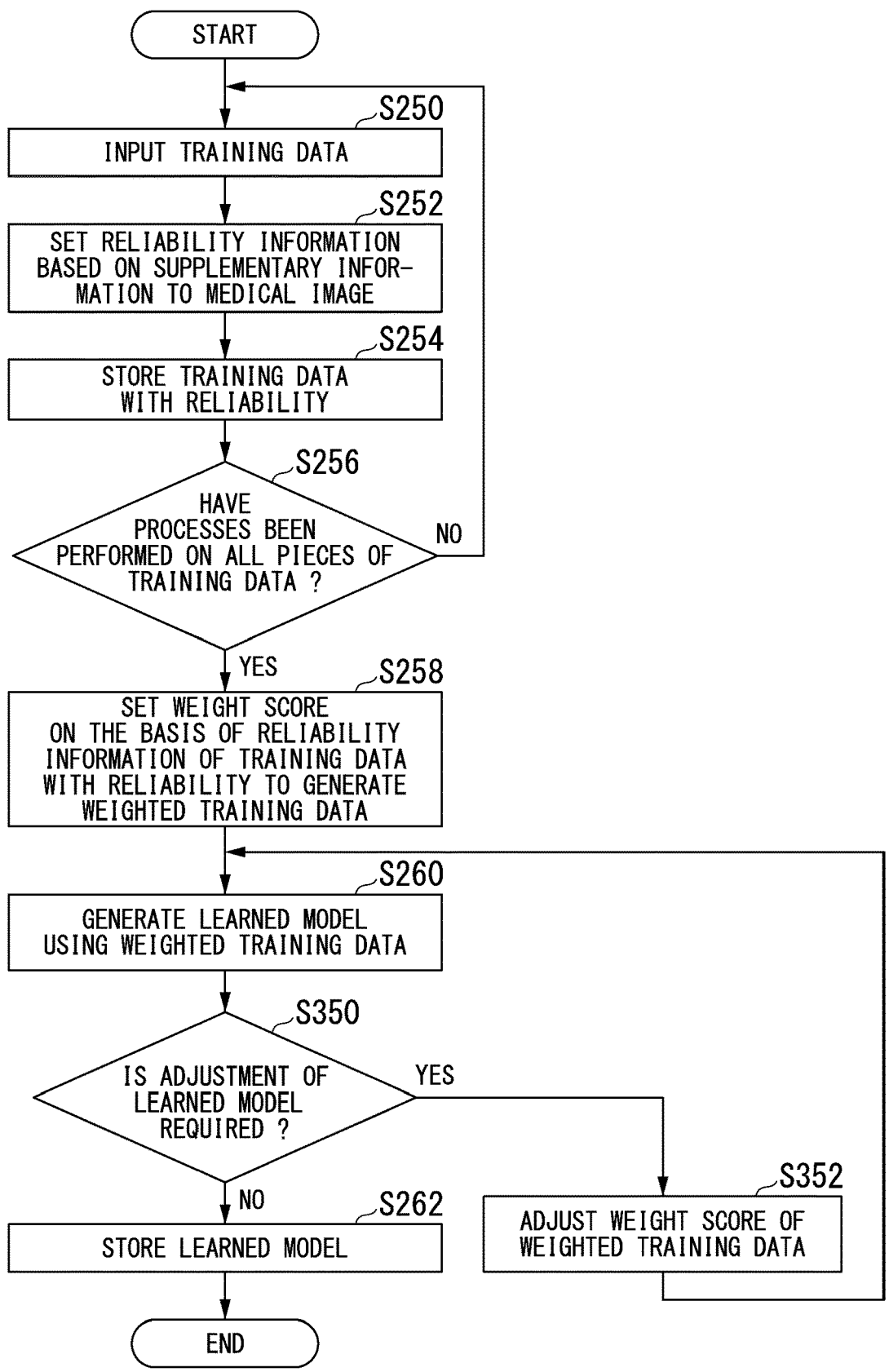
FIG. 16 is a flowchart showing a flow of a series of processes of a processing circuit of the information processing server of the third embodiment.

FIG. 16 is a flowchart showing the flow of a series of processes of the processing circuit 240B of the information processing server 200B of the third embodiment. The processes of FIG. 16 differ from the above-described processes of FIG. 14 in that processes of steps S350 and step S352 are added. Accordingly, the following description will chiefly focus on the processes of step S350 and step S352.

After the process of step S260 ends, the adjustment function 248 determines whether adjustment of correction of the learned model is required (step S350). When it is determined that correction of the learned model is required, the adjustment function 248 adjusts weights of weighted training data and returns to the process of step S260. Further, when it is determined that correction of the learned model is not required, the adjustment function 248 stores the learned model in the memory 250A (step S262) and ends the processes of this flowchart.

Meanwhile, the adjustment function 248 may adjust weight scores of the weighting table in the process of step S352. In this case, the flow returns to the process of step S258 after the process of step S352. Further, the adjustment function 248 may perform a process of excluding weighted training data in which values of operation situation scores or creator information scores are equal to or less than a predetermined value as input data for learning in the learning function 246 in the process of step S352.

According to the above-described third embodiment, it is possible to adjust weight scores and inputs of training data to acquire more appropriate learning results in addition to obtaining the same effects as those of the first and second embodiments. Meanwhile, each of the above-described first to third embodiments may be combined with some or all of other embodiments. In addition, in each of the above-described embodiments, although the information processing server 200 (200A, 200B) is connected to the medical institution terminal 100 (100A) through the network NW in the medical image processing system 1 (2), the present invention is not limited thereto and they may not be connected to the network NW. For example, when the information processing server 200 can access data in the memory 150 of the medical institution terminal 100, it is possible to acquire information necessary for the processes of the present embodiment from the medical institution terminal 100 by storing the data in the medical institution terminal 100 in a portable storage medium such as a universal serial bus (USB) memory and reading the aforementioned data through the information processing server 200 from the storage medium. Further, the medical institution terminal 100 can acquire information with respect to the processes of the present embodiment from the information processing server 200 using the same technique.

Any of the above-described embodiments can be represented as follows.

A medical image processing apparatus including:

a storage configured to stores a program; and a processor, wherein the processor is configured to, by executing the program:

acquire training data created by a creator on the basis of medical image;

set, to the acquired training data, reliability information based on a creation situation of the training data or information about the creator who has created the training data; and generate a learned model using the training data according to weighting based on the set reliability information.

According to at least one of the above-described embodiments, it is possible to clarify the quality of training data by including the training data creation function 142 for acquiring training data of a medical image and the reliability setting function 144 for setting, to the training data acquired through the training data creation function 142, reliability information based on one or both of a creation situation of the training data and information on a creator who has created the training data in the medical image processing apparatus. In addition, according to the first embodiment, it is possible to acquire a more appropriate learned model and learning results by adding the quality of training data thereto.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to:
acquire training data created by a creator on the basis of a medical image;
set, to the training data, reliability information based on a creation situation of the training data or information about the creator who created the training data; and
generate a learned model using the training data according to weighting based on the set reliability information,
wherein the information about the creator includes, among information about qualifications possessed by the creator with respect to a medical field and information about a busyness degree of the creator, at least the information about the busyness degree,
wherein the qualifications indicates that the creator has a specific technique in a special field,
wherein the busyness degree is represented by a value set based on a result of a reply from an operator to an inquiry about busyness.

2. The medical image processing apparatus according to claim 1, wherein the processing circuitry is further configured to:
receive an input operation of an operator; and
cause a display to display the medical image,
wherein the processing circuitry acquires the training data generated on the basis of the input operation in a state in which the display displays the medical image.

3. The medical image processing apparatus according to claim 1, wherein the processing circuitry acquires a creation time of the medical image or the training data, and sets the reliability information indicating reliability of the medical image or the training data, the reliability of the medical image or the training data increasing as the creation time becomes later.

4. The medical image processing apparatus according to claim 1, wherein the training data includes at least one of presence or absence of a lesion with respect to the medical image, identification of a lesion type and designation of a specific region.

5. The medical image processing apparatus according to claim 1, wherein the creation situation includes information about awareness of the creator.

6. The medical image processing apparatus according to claim 5, wherein the information about the awareness includes one or both of a time required for creation of the training data by the creator and a confidence degree with respect to creation of the training data.

7. The medical image processing apparatus according to claim 1, wherein the processing circuitry is further configured to:
cause a display to display an image; and
receive an input from an operator,
wherein the processing circuitry causes the display to display an input screen through which the operator inputs the reliability information.

8. The medical image processing apparatus according to claim 1, wherein the processing circuitry sets weight scores on the basis of items included in the creation situation and the information about the creator.

9. The medical image processing apparatus according to claim 1, wherein the processing circuitry sets a weight score for a combination of a plurality of items included in the creation situation and the information about the creator.

10. The medical image processing apparatus according to claim 8, wherein the processing circuitry generates the learned model on the basis of the weight scores.

11. The medical image processing apparatus according to claim 8, wherein the processing circuitry is further configured to:
adjust weight scores set to the training data,
wherein the processing circuitry adjusts weights set to the training data when a guideline associated with details of the training data has been changed.

12. The medical image processing apparatus according to claim 11, wherein the processing circuitry excludes, the training data in which the weight scores are equal to or less than a predetermined value from among a plurality of pieces of the training data set weight scores.

13. The medical image processing apparatus according to claim 11, further comprising a storage configured to stores the training data to which the weight scores are set,
   wherein the processing circuitry deletes, from the storage, the training data in which the weight scores are equal to or less than a predetermined value from among a plurality of pieces of the training data stored in the storage.

14. A medical image processing method, using a computer of a medical image processing apparatus, comprising:
   acquiring training data created by a creator on the basis of a medical image;
   setting, to the training data, reliability information based on a creation situation of the training data or information about the creator who created the training data; and
   generating a learned model using the training data according to weighting based on the set reliability information,
   wherein the information about the creator includes, among information about qualifications possessed by the creator with respect to a medical field and information about a busyness degree of the creator, at least the information about the busyness degree,
   wherein the qualifications indicating that the creator has a specific technique in a special field,
   wherein the busyness degree being represented by a value set based on a result of a reply from an operator to an inquiry about busyness.

15. A computer readable non-transitory storage medium storing a program causing a computer of a medical image processing apparatus:
   to acquire training data created by a creator on the basis of a medical image;
   to set, to the training data, reliability information based on a creation situation of the training data or information about the creator who created the training data; and
   to generate a learned model using the training data according to weighting based on the set reliability information,
   wherein the information about the creator includes, among information about qualifications possessed by the creator with respect to a medical field and information about a busyness degree of the creator, at least the information about the busyness degree,
   wherein the qualifications indicating that the creator has a specific technique in a special field,
   wherein the busyness degree being represented by a value set based on a result of a reply from an operator to an inquiry about busyness.

16. The medical image processing apparatus according to claim 1,
   wherein the processing circuitry queries the creator about the busyness after the creator created the training data.

* * * * *